United States Patent [19]

Tamura et al.

[11] Patent Number: 4,884,290

[45] Date of Patent: Nov. 28, 1989

[54] METHOD OF ANALYZING COMPOSITION OF OPTICAL FIBER BASE MATERIAL TO BE MEASURED BY RADIOACTIVE RAYS

[75] Inventors: Junichi Tamura; Ryoichi Hara; Fumihiko Abe; Hisashi Koaizawa, all of Ichihara, Japan

[73] Assignee: The Furukawa Electric Company, Ltd., Tokyo, Japan

[21] Appl. No.: 786,695

[22] Filed: Oct. 11, 1985

[30] Foreign Application Priority Data

Oct. 13, 1984 [JP] Japan ................... 59-214580

[51] Int. Cl.[4] .................................. G01T 1/36
[52] U.S. Cl. ........................ 378/83; 378/85; 378/53; 378/54; 250/358.1
[58] Field of Search .............. 378/51, 53–56, 378/82–85, 45, 88; 250/358.1, 362

[56] References Cited

U.S. PATENT DOCUMENTS

| | | | |
|---|---|---|---|
| 3,004,163 | 10/1961 | Edholm | 378/53 |
| 3,100,261 | 8/1963 | Bigelow | 378/53 |
| 3,160,747 | 12/1964 | De Vries | 378/85 |
| 3,261,911 | 7/1966 | Bailey et al. | 378/51 |
| 3,354,308 | 11/1967 | Engel et al. | 378/54 |
| 3,375,369 | 3/1968 | Goldman et al. | 378/53 |
| 3,397,312 | 8/1968 | Okano | 378/85 |
| 3,435,220 | 3/1969 | Hanken | 378/53 |
| 3,832,550 | 8/1974 | Bartlett et al. | 378/56 |
| 3,904,876 | 9/1975 | Arendt | 378/53 |
| 3,944,830 | 3/1976 | Dissing | 378/55 |
| 3,956,633 | 5/1976 | Honnsfield | 250/362 |
| 4,317,994 | 3/1982 | Mallozzi et al. | 378/53 |
| 4,472,825 | 9/1984 | Jenkins | 378/83 |
| 4,567,605 | 1/1986 | Bartels | 378/85 |

FOREIGN PATENT DOCUMENTS 0441488  8/1974  U.S.S.R. .................... 378/85

Primary Examiner—Craig E. Church
Assistant Examiner—John C. Freeman
Attorney, Agent, or Firm—Foley & Lardner, Schwartz, Jeffery, Schwaab, Mack, Blumenthal & Evans

[57] ABSTRACT

A method of analyzing a composition of an optical fiber base material to be measured by radioactive rays, which comprises the steps of irradiating radioactive rays from a radiation generator to the composition containing a plurality of elements or the substance, emitting the transmitted rays of the base material to a plurality of single crystals to produce several types of transmitted rays of specific energy, and measuring the transmitted rays by a radiation detector to analyze the compositions of the constituent elements in the base material. Thus, this method can accurately and economically analyze the composition in response to the constituent elements of the composition and the thickness of the composition.

12 Claims, 2 Drawing Sheets

METHOD OF ANALYZING COMPOSITION OF OPTICAL FIBER BASE MATERIAL TO BE MEASURED BY RADIOACTIVE RAYS

BACKGROUND OF THE INVENTION

This invention relates to a method of analyzing a composition of an optical fiber base material to be measured by nondestructive means utilizing radioactive rays.

When the ratio of elements contained in a substance which includes a plurality of elements and the absolute amounts of the elements are obtained by nondestructive means in the substance, a method of analyzing the substance by the steps of irradiating a plurality of monochromatic X-rays to the substance, and measuring the intensities of the transmitted X-rays by a predetermined detecting system is employed.

In addition, a detector having semiconductor elements of Ge or Si is generally used as a detecting system for accurately analyzing the substance.

In the above-mentioned method by the X-rays, the energy of the X-rays is initially determined. Thus, the energy of the generated X-rays cannot be freely varied, and the thickness of the substance to be measured and the accurate analysis responsive to the constituent elements cannot be determined. Furthermore, the detecting system generally employs a detector made of semiconductor elements of Ge and the like, but the Ge detector is expensive, and must be used while cooling with liquefied nitrogen. Thus, the maintenance and the management of the system have difficulties.

On the other hand, in a semiconductor detector mode of Si, the resolution of the energy is excellent, but this is also expensive and must be cooled by liquefied nitrogen. Thus, this detector cannot be conveniently used.

SUMMARY OF THE INVENTION

Accordingly, an object of this invention is to provide a method of analyzing a composition of an optical fiber base material to be measured by radioactive rays, which can eliminate the aforementioned drawbacks and disadvantages and accurately and economically analyze the composition in response to the constituent elements of the composition and the thickness of the composition.

According to this invention, there is provided a method of analyzing a composition of an optical fiber base material to be measured by radioactive rays, which comprises the steps of irradiating radioactive rays from a radiation generator to the composition containing a plurality of elements or the substance, emitting the transmitted rays of the base material to a plurality of single crystals to produce several types of transmitted rays of specific energy, and measuring the transmitted rays by a radiation detector to analyze the compositions of the constituent elements in the base material.

According to the method of this invention, the rays transmitted through the base material to be measured, i.e., the transmitted rays, are emitted to the plurality of single crystals to produce a plurality of transmitted rays of specific energy. Thus, the energy of the rays to be produced in response to the thickness of the base material to be measured and the constituent elements can be freely altered. Therefore, the analyzing accuracy of the transmitted rays when measuring and analyzing the transmitted rays by the radiation detector can be enhanced, while the detector need not be made of a semiconductor detector of Ge or Se, but may be made of an inexpensive and readily handled scintillation counter tube, and the difficulty in handling can be eliminated and the detector is economic.

The above and other related objects and features of the invention will be apparent from a reading of the following description of the disclosure found in the accompanying drawings and novelty thereof pointed out in the appended claims.

DESCRIPTION OF THE PREFERRED EMBODIMENTS

Embodiments of a method of analyzing a composition of an optical fiber base material by radioactive rays according to this invention will be described with reference to the accompanying drawings.

Figures 1A, 1B:
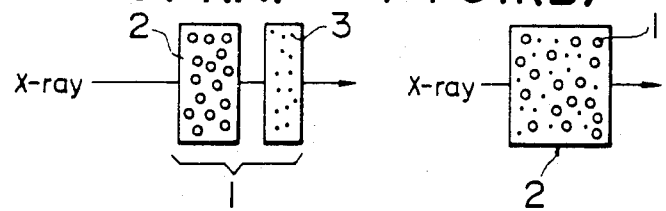
FIGS. 1(a) and 1(b) are explanatory views schematically showing various states of base materials to be measured according to a method of analyzing a composition of an optical fiber base material by radioactive rays of the present invention.

FIGS. 1(a) and 1(b) show the state of the base material to be measured according to the method of this invention. In FIG. 1(a), a substance 2 made of one type of element and a substance 3 made of another different type of element are aligned adjacent to each other in the base material 1 to be measured, and in FIG. 1(b), the base material 1 made of a plurality of elements is provided.

Figure 2A:
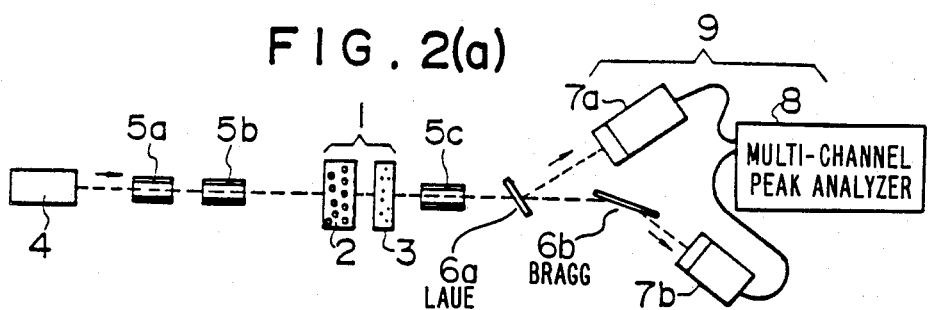
FIGS. 2a–2d are explanatory views schematically showing embodiments of the present invention in which energy spectral analysis comprises a sequence of Laue-Bragg, Laue-Laue, Bragg-Bragg, and Bragg-Laue, respectively.

FIG. 2(a) shows an embodiment of this invention of a method of analyzing a composition of an optical fiber base material to be measured by radioactive rays.

In FIG. 2, reference numeral 4 designates a radiation generator, which, for example, employs an X-ray generator.

Reference numerals 5a, 5b and 5c denote collimators, and reference numerals 6a and 6b denote single crystals.

Reference numerals 7a and 7b designate detectors made of scintillation counter tubes which, for example, employ NaI as a scintillator, numeral 8 designates a multichannel type peak analyzer. A radiation detector 9 is composed by connecting the both detectors 7a, 7b to the analyzer 8.

The scintillation counter tube for the detectors 7a and 7b is not limited to that which employs NaI as the scintillator, but may use CsI(Tl), KI(Tl), or LiI(Tl) as the scintillator. The peak analyzer 8 is not limited to the multichannel type, but may employ a single channel in combination.

In FIG. 2(a), when the composition of the base material 1 to be measured of FIG. 1(a) is analyzed, the base material 1 to be measured is disposed between the collimators 5b and 5c.

After the radioactive rays (X-rays) from the radiation generator 4 are transmitted through the collimators 5a, 5b, the rays are incident to the base material 1 to be measured, transmitted through the base material 1, i.e., the transmitted rays are incident on the single crystals 6a, 6b, and the diffracted waves are then incident on the detectors 7a, 7b.

The single crystal 6a is disposed to produce the desired energy which satisfies the Laue conditions, and the other single crystal 6b is regulated at the angle of the crystal to satisfy the Bragg conditions to produce the desired energy.

Figure 2B:
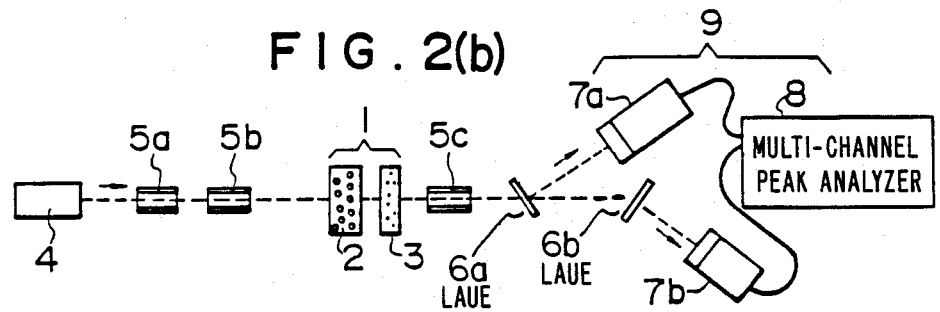
Figure 2C:
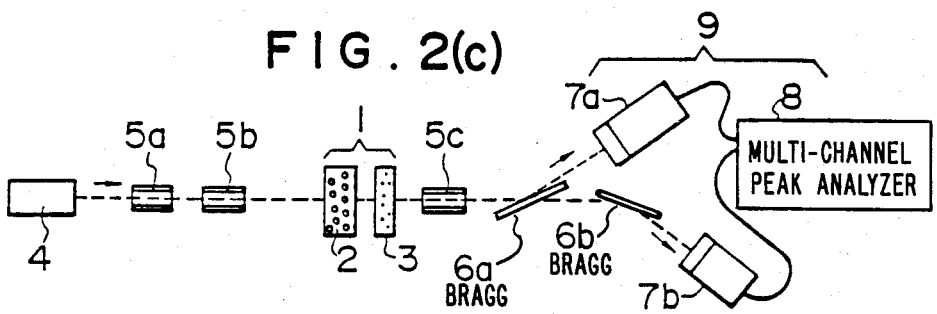
Figure 2D:
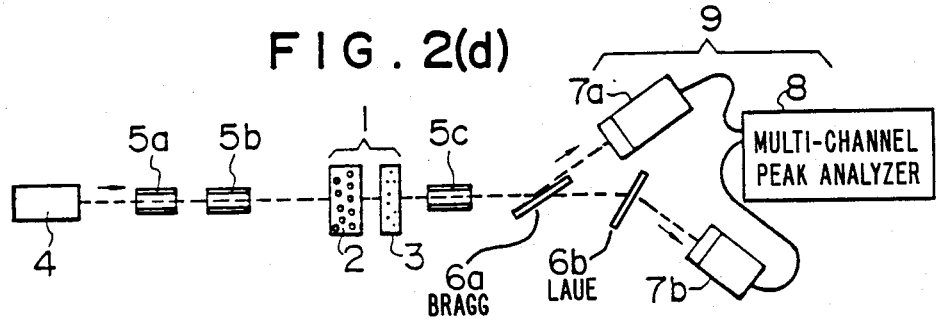

The energy spectral analysis may include not only a combination of the sequence of Laue and Bragg, but of Laue-Laue, Bragg-Bragg as shown in FIGS. 2b–2d or Bragg-Laue.

The energy spectral analysis by Laue and Bragg will be described with reference to FIGS. 3(a) and 3(b).

Figures 3A, 3B:
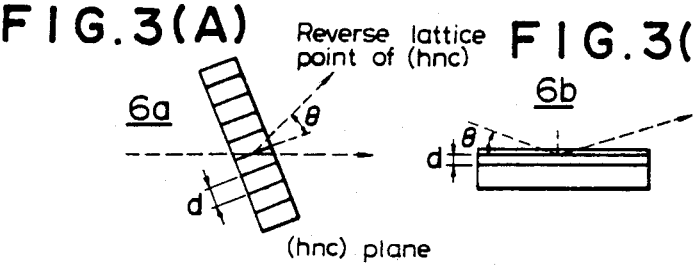
FIGS. 3(a) and 3(b) are explanatory views showing a Laue case and a Bragg case by X-ray diffraction in the method according to this invention.

In the Laue case shown in FIG. 3(a) and the Bragg case shown in FIG. 3(b), the transmitted rays (X-rays) incident as shown in FIG. 3(a) and 3(b) are diffracted in the lattice plane in the crystal, and the X-rays produced from the surface are different from the incident wave side.

In any case, when the distance between the lattice planes is represented by d, the energy E produced through the single crystals 6a, 6b is as below.

$$E = nhc/2d \sin\theta$$

In the above equation, n represents an integer number, h represents Planck's constant, c represents the velocity of a light, and $\theta$ represents an angle formed between the X-rays and the lattice plane.

Therefore, the X-ray having desired energy can be produced by altering the angle $\theta$.

As described above, the transmitted rays (X-rays) incident to the detectors 7a, 7b are irradiated to the scintillator (NaI) of the detectors 7a, 7b, lose their energy, and emit lights.

The lights are amplified by a photoelectric multiplier, introduced into the multichannel peak analyzer 8, and can be analyzed at the peak to known the intensity distribution of the X-rays.

As a simple example, a method of obtaining the mass thicknesses of the substances 2 and 3 in the base material 1 to be measured by the intensities of the X-rays measured as described above will be described in detail.

The mass thicknesses are values obtained by the product of the thickness of the base material (the size of the direction for transmitting the radioactive rays) and the density of the element in the thicknesswise direction, thereby clarifying the ratio of the compositions and the absolute weights of the constituent elements in the base material to be measured.

In the abovementioned example, the incident X-rays are represented by I0, the energies produced through the single crystals 6a, 6b are E1, E2, the intensities of the transmitted X-rays are I1, I2, the absorption coefficients of the substances 2, 3 to the energies E1, E2 are MA1, MA2, MB1, MB2, and the thicknesses of the substances 2, 3 in the radioactive ray transmitting direction are 1A, 1B. Then, the following equations are obtained.

$$I1 = I0 e^{-\left(\frac{MA1}{\rho A} \cdot \rho A l A + \frac{MB1}{B} \cdot \rho B l B\right)}$$

$$I2 = I0 e^{-\left(\frac{MA2}{\rho A} \cdot \rho A l A + \frac{MB2}{\rho B} \cdot \rho B l B\right)}$$

Figure 4:
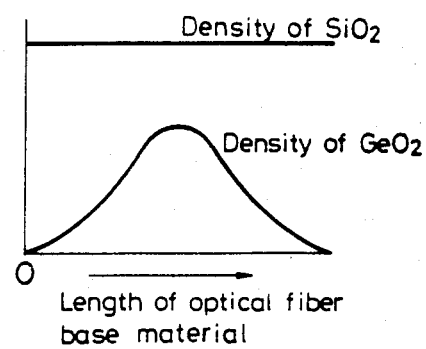
FIG. 4 is a distribution view of the densities of elements of the base material to be measured.

When the mass thickness ($\rho l$) is obtained from these equations, the following equations will be gained.

$$\rho B l B = \frac{(MA1 H2 - MA2 H1)\rho B}{\begin{vmatrix} MA1 & MB1 \\ MA2 & MB2 \end{vmatrix}}$$

$$\rho A l A = \frac{(MB2 H1 - MB1 H2)\rho A}{\begin{vmatrix} MA1 & MB1 \\ MA2 & MB2 \end{vmatrix}}$$

Where $$H1 = \ln\frac{I0}{I1}, \quad H2 = \ln\frac{I0}{I2},$$

and $\rho A$, $\rho B$ are the densities of the substances 2 and 3. The above method can obtain the mass thicknesses of the respective elements of the base material to be measured containing two types of elements as shown in FIG. 4 such as, for example, $SiO_2$ and $GeO_2$.

The substance or base material to be measured may be circular, polygonal or any arbitrary shape in cross section.

For example, in a cylinder or a cylindrical post formed of two types of elements, in which the mass thicknesses of the respective elements are symmetrically distributed with respect to the central axis, the substance to be measured and the direction of irradiating the X-rays are crossed perpendicularly, and the substance to be measured is moved in the direction perpendicular to the X-ray irradiating direction, or the radiation generator and the radiation detector are moved, and the X-ray is scanned from one side end to the other side end of the substance to be measured.

In this case, the intensity of the X-rays transmitted through the irradiating position is sequentially detected by the detector (scintillation counter tube) in the same manner as the abovementioned method, thereby obtaining the mass thicknesses of the constituent elements with respect to the lateral direction of the substance to be measured on the basis of the detected result.

According to the method of the present invention, the radiation except the X-rays may be employed.

According to this invention as described above, when the substance or base material to be measured contains a plurality of elements or substances are nondestructively measured by arbitrary radioactive rays, the rays transmitted through the substance to be measured are emitted to a plurality of single crystals to produce a plurality of types of the transmitted rays of the specific energy. Thus, the energy of the radioactive rays to be produced will be freely altered in response to the thickness of the substance to be measured and the constituent elements, and the analyzing accuracy of the measuring analysis with transmitted rays by the radiation detector can be accordingly enhanced, the detector may be performed by a scintillation counter tube which is inexpensive and easily handled.

What is claimed is:

1. A method of analyzing a composition of an optical fiber base material to be measured by x-rays, comprising the steps of:
   irradiating x-rays from a radiation generator to the base material contining a plurality of elements
   emitting x-rays from the base material along a line of passage,
   placing a plurality of single crystals so as to intersect said line of passage, and wherein each of said crystals is independently positioned with respect to each other,
   producing from each crystal an X-ray beam of specific energy, and
   measuring each X-ray beam of specific energy with a separate radiation detector for each single crystal to analyze the compositions of the plurality of elements in the base material.

2. The method according to claim 1, wherein the base material is scanned by the irradiated x-rays as the x-rays are emitted.

3. The method according to claim 1, further including the steps of:
   diffracting, at the plurality of single crystals, the x-rays emitted from the base material to produce several beams of x-rays of specific energy; and
   directing the x-rays of specific energy to a radiation detector.

4. The method according to claim 1, wherein one single crystal of the plurality of single crystals is disposed to produce a desired energy which satisfies Laue diffraction conditions, and another single crystal is disposed to produce a desired energy which satisifes Bragg diffraction conditions.

5. The method according to claim 4, an energy spectral analysis of the emitted x-rays comprises sequentially producing Laue diffraction x-rays of said desired energy and Bragg diffraction x-rays of said desired energy.

6. The method according to claim 1, wherein an energy spectral analysis of the emitted x-rays comprises sequentially producing first Bragg diffraction x-rays of a desired energy and second Bragg diffraction x-rays of a desired energy.

7. The method according to claim 4, wherein an energy spectral analysis of the emitted x-rays comprises sequentially producing Bragg diffraction x-rays of a desired energy and Laue diffraction x-rays of a desired energy.

8. The method according to claim 1, wherein the base material is moved through the emitted x-rays.

9. A method of analyzing a composition of an optical fiber base material to be measured by x-rays, comprising the steps of:
   irradiating x-rays from a radiation generator to the base material containing a plurality of elements,
   emitting x-rays from the base material along a line of passage,
   placing a plurality of single crystals so as to intersect said line of passage producing from each crystal an x-ray beam of specific energy which was formed due to Laue diffraction, and
   measuring the intensity of each x-ray of specific energy with a radiation detector corresponding to each crystal to analyze the compositions of the plurality of elements in the base material,
   wherein an energy spectral analysis of the emitted x-rays comprises sequentially producing first Laue diffraction x-rays of a desired energy and second Laue diffraction x-rays of a desired energy.

10. The method according to claim 9, further including the steps of:
    diffracting, at the plurality of single crystals, the x-rays emitted from the base material to produce several beams of x-rays of specific energy; and
    directing the x-rays of specific energy to a radiation detector.

11. The method according to claim 9, wherein the base material is moved through the emitted x-rays.

12. The method according to claim 9, wherein the base material is scanned by the emitted x-rays.

* * * * *